United States Patent [19]
Sakr et al.

[11] Patent Number: 5,958,873
[45] Date of Patent: Sep. 28, 1999

[54] ORAL FORMULATION FOR TREATMENT OF BACTERIA-INDUCED DISEASES OF THE COLON

[75] Inventors: Ahmed Adel Sakr; Walid Abdel-Azim Habib, both of Cincinnati, Ohio

[73] Assignee: University of Cincinnati, Cincinnati, Ohio

[21] Appl. No.: 08/950,224

[22] Filed: Oct. 14, 1997

Related U.S. Application Data

[60] Provisional application No. 60/049,236, Jun. 9, 1997.
[51] Int. Cl.$^6$ .............................. A61K 38/00; C07K 5/00; C07K 7/00
[52] U.S. Cl. .................................... 514/2; 514/12
[58] Field of Search ............................. 514/2, 12

[56] References Cited

FOREIGN PATENT DOCUMENTS 9313793  7/1993  WIPO .............................. A61K 37/02

OTHER PUBLICATIONS

Lamb et al., *Essentials of Physiology*, 1980, Blackwell Scientific Publications, Oxford; pp. 161–162.

*Primary Examiner*—Avis M. Davenport
*Attorney, Agent, or Firm*—Frost & Jacobs LLP

[57] ABSTRACT

The invention is directed to lanthocin-containing tablet formulations for oral administration. The inventive formulations afford delivery of the lanthocin to the colon in amounts sufficient to treat diseases brought on by bacterial infection of the colon. Also provided is a process for preparation of the formulations.

18 Claims, 11 Drawing Sheets

FIGURE 2

Effect of Eudragit L30D Coat Thickness on Time to Beginning of Disintegration of Nisin Tablets in Phosphate Buffer pH 6.8 (Linear Regression)

Dissolution of Coated Tablet at 37$^0$C, pH 6.8, 50 mM Phosphate

FIGURE 6A

Delivery of Nisin to the Colon in a Tablet of 40% Coat Thickness

FIGURE 7B

Delivery of Nisin to the Colon
in a Tablet of 120% Coat Thickness

ORAL FORMULATION FOR TREATMENT OF BACTERIA-INDUCED DISEASES OF THE COLON

CROSS-REFERENCE TO RELATED APPLICATIONS

This application claims the benefit, under 35 U.S.C. § 119(e), of U.S. Provisional Patent Application Ser. No. 60/049,236, filed Jun. 9, 1997.

BACKGROUND OF THE INVENTION

Nisin is a bacteriocin, an antimicrobial substance produced by a food grade organism, and is a member of a group of similar substances referred to as lantibiotics (or lanthocins herein) and which among others include subtilin, epidermin, gallidermin and pep 5.

Nisin is produced by *Lactococcus lactis* subsp. *Lactis* belonging to the Lancefield serological group N [Mattick, A. T. R. and A. Hirsch, 1947 Lancet. 2, 5]. Nisin is a peptide comprised of 34 amino acid residues and contains five ring structures cross-linked by thioether bridges that form lanthionine or B-methyllanthionine. These thioethers result from the condensation of cysteine sulfhydryl groups with dehydro side chains formed from either serine or threonine residues as a result of post-translational modifications of a nisin precursor peptide.

It has been reported that nisin acts as a cationic surface active agent and that its activity can be neutralized by anionic detergents [Ramseier, H. R. 1960 Arch. Mikrobiol, 37, 57], and at a molecular level that nisin acts at the cytoplasmic membrane and inhibits peptidoglycan biosynthesis [Reisinger et al. 1980 Arch. Microbiol. 127, 187]. The action of nisin against vegetative bacteria is most likely the result of voltage dependent depolarization of the plasma membrane following insertion of the peptide into the lipid bilayer, possibly through the interaction of adjacent nisin molecules to form a transient pore or channel. The molecular properties of nisin and the mechanism of its biosynthesis have been the subject of a recent review [Jung, G. and H. G. Sahl 1991 Nisin and Novel Lantibiotics ESCOM Science Publishers, Leiden].

Nisin is considered to have a narrow spectrum of activity and generally is only active against certain Gram positive bacteria, except when combined with a chelating agent when nisin is surprisingly active against Gram negative bacteria and exhibits enhanced activity against Gram positive bacteria (U.S. Pat. Nos. 5,217,950 and 5,260,271 to Blackburn et al.). Nisin has been used as an antimicrobial food preservative and is accepted as safe by JEFCA and various national authorities regulating the use of food additives including those of the USA, UK and EEC.

Although nisin was shown to be effective in preliminary animal model studies [Mattick, A. T. R. and A. Hirsch, 1947 Lancet. 2:5; Bavin, E. M., et al., 1952 Lancet 1:127; Gowans, J. L., et al. 1952 Brit. J. Pharmacol. 7:438; Hirsch, A. and A. T. R. Mattick, 1949 Lancet ii:190], nisin was found to be insufficiently useful to be developed therapeutically in human or veterinary medicine.

*Clostridium difficile* is an anaerobic Gram-positive, spore-forming toxigenic bacillus, infrequently found in significant numbers in the colon of humans. However, because it is refractory to a number of antimicrobial agents and is endemic in hospitals and nursing homes, it can appear when the normal bacterial flora of the colon is suppressed, most often after treatment with broad-spectrum antibacterial agents. Under these circumstances, *C. difficile* can cause severe diseases, known as antibiotic-associated diarrhea and pseudomembranous colitis. Treatments for these disorders include metronidazole and oral vancomycin. Currently, however, the use of vancomycin is being actively discouraged because, particularly in an oral form, it selects for a new class of highly resistant intestinal organisms, vancomycin-resistant enterococci (VRE), which can cause fatal, untreatable infections at other body sites. Metronidazole is not active against enterococci, so its use may also contribute to selection of VRE in the colon. The relapse rate for *C. difficile* disease is very high, about 20%; it is thought that this may be related to the formation of spores, which are difficult to eradicate.

BRIEF DESCRIPTION OF THE INVENTION

The object of the invention is to provide a means of treating bacteria-induced diseases of the colon and to eradicate potentially dangerous bacteria colonizing the colon. To this end, the unexpected stability in the colon, and nontoxicity when administered in large doses to the colon, of lanthionine-containing bacteriocins (lanthocins) such as nisin have been demonstrated. As a consequence of this discovery, a further object of the invention is to provide a means of delivering the lanthocin of choice to the colon in sufficient quantity to effectively treat the colonic infection.

DETAILED DESCRIPTION OF THE INVENTION

An object of the invention is to provide means of treatment of *C.-difficile*—associated diseases of the colon and ridding the large intestine of colonizing organisms such as VRE.

To this effect, we have found that nisin has potent activity against pathogenic strains of various Gram-positive bacteria, including VRE (U.S. application Ser. No. 08/667,650, incorporated herein in its entirety by reference). Nisin was known to have activity against food spoilage organisms of the genus Clostridium, and, after our initial discovery of its activity against *C. difficile*, such activity was recently disclosed [Kerr, et al., 1997 Lancet 349:1026]. Herein we demonstrate that nisin has particularly potent activity against a large number of clinical isolates of *C. difficile*, including strains resistant to clindamycin and metronidazole. Also, nisin is shown to have little activity against the predominant normal bowel flora of humans, *Bacteroides fragilis*. In fact the window between concentrations of nisin active against 50% of *C. difficile* strains and concentrations active against 50% of *B. fragilis* is very large. This means that, contrary to the teaching of Kerr, et al., effective dosages of nisin are unlikely to have an adverse effect on protective commensal bacteria in the bowel. Although, as already stated, nisin requires potentiators for activity against most Gram-negative bacteria, there are some exceptions. For example, fastidious Gram-negatives, such as *Neisseria gonorrhoeae*, are susceptible to nisin alone. *B. fragilis* is a fastidious anaerobe, and it was not previously known what its susceptibility to nisin would be.

Figure 1:
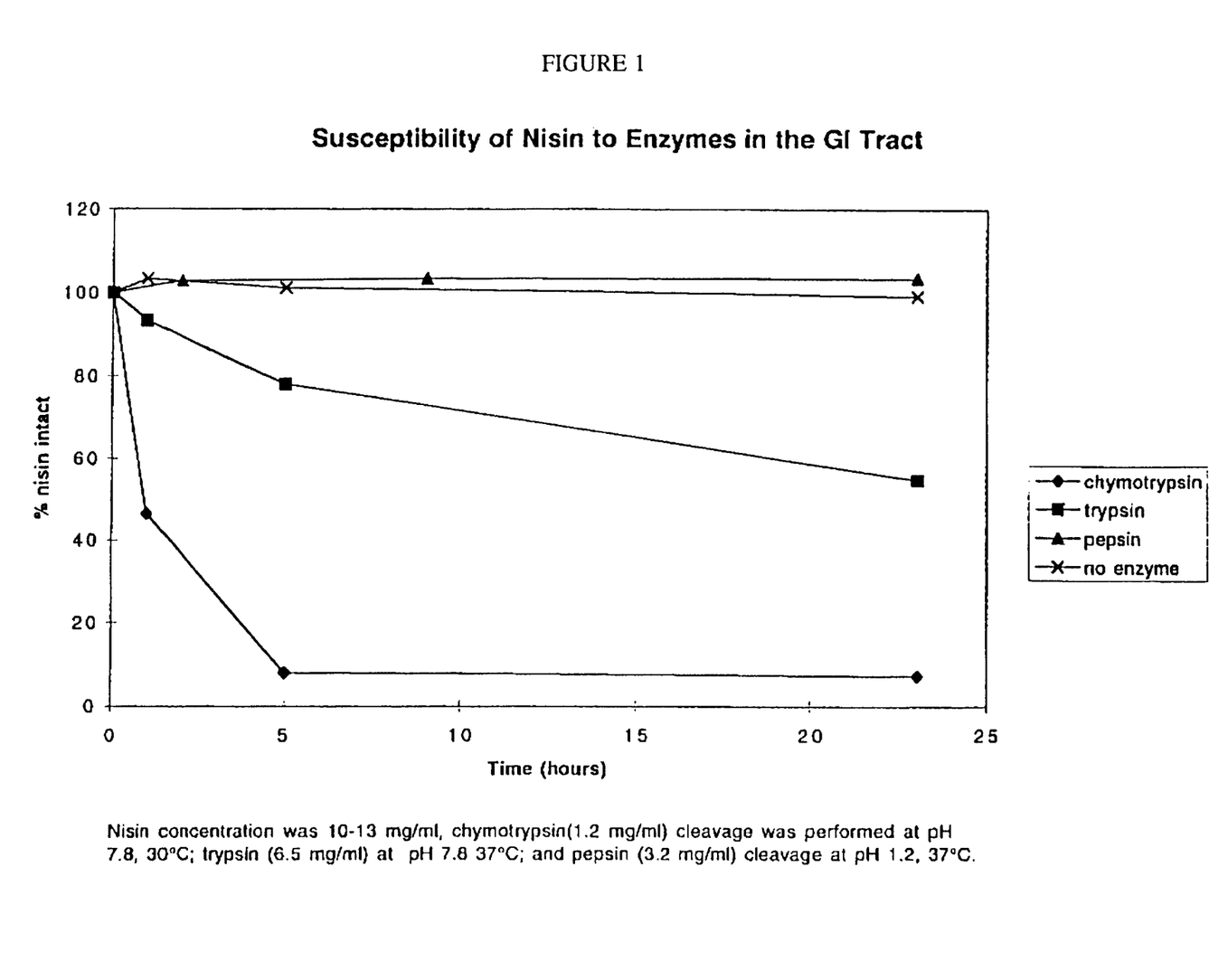
FIG. 1 shows the susceptibility of nisin to enzymes found in the gastrointestinal tract.

Because nisin is a peptide and can be digested by proteolytic enzymes, which are present in large amounts in the small intestine (cf. FIG. 1), its oral use to target infections of the lower gastrointestinal tract has not been previously considered. Furthermore, it was not known whether intact nisin would be tolerated if it were to be delivered to the lower gastrointestinal tract, nor whether sufficient stability to promote antimicrobial activity could be expected at that site.

We have now demonstrated, using animal models, that nisin is not irritating to the colon when delivered repeatedly in a sub-acute intracolonic toxicity study. Furthermore, we have demonstrated that intact nisin cannot be detected in the blood of animals so treated, suggesting that systemic absorption (and possible systemic toxicity) is unlikely to occur by this route. Additionally, in an animal study in which a portion of the colon was ligated, it was demonstrated that a significant proportion of nisin remained intact in situ for several hours after being instilled into the colon.

It is therefore of potential practical use to develop systems for delivering nisin, or other lanthocin antimicrobial peptides, including structural variants of these molecules produced by genetic engineering or by semi-synthetic chemistry, to treat infections of the colon caused by microorganisms (including, but not limited to, *C. difficile*) susceptible to these peptides or to rid the large intestine of susceptible colonizing organisms (including, but not limited to, VRE) that present a potential hazard to the health of the individual or to other patients. Accordingly, another aspect of the invention is the development of formulations which allow delivery by oral administration of amounts of nisin effective to treat bacterial infection in the colon.

Pharmaceutical formulations of these peptides would include appropriately coated tablets or granules or capsules for oral administration that afford maintenance of the integrity of the dosage form during passage through the stomach and small intestine and that then permit release of the active ingredient in the proper region of the gastrointestinal tract (lower small intestine to upper large intestine). However, it is envisioned that suppositories and enemas, for example, may also serve as effective dosage forms. The specific dosage forms set forth below are merely by way of example and are not intended to limit the scope of the invention in any way.

EXAMPLES

Examples 1–5 are concerned with the testing of the properties of nisin in the environment of the colon and the effectiveness of nisin against bacteria normally residing therein.

Example 1a

Activity of Nisin against *C. difficile*

Twenty clindamycin-resistant clinical isolates from McGuire Veterans' Administration Hospital, Richmond, Va. were tested in Brucella agar with sheep's blood under anaerobic conditions. The MIC (minimal inhibitory concentration) was defined as the lowest concentration tested that completely inhibits visible growth of the bacteria.

As shown in Table 1, all strains were inhibited by 0.25 µg/ml or less of nisin.

Sixty clinical isolates from the University of Florence (Italy) hospital were tested for susceptibility to nisin and to antimicrobial agents currently used to treat *C. difficile* diarrhea and colitis, using the same methods described above. As shown in Table 2, the median MIC, or $MIC_{50}$ (the concentration at which the growth of 50% or more of the test strains was inhibited), of nisin for these strains was 0.05 µg/ml, significantly lower than the amount of vancomycin or metronidazole needed to inhibit the same strains. $MIC_{90}$ values are the concentrations of antibacterial at which the growth of 90% or more of the test strains was inhibited.

This example demonstrates that *C. difficile* is a suitable target organism for therapy with nisin or related peptides.

Example 1b

Lack of Activity of Nisin against *Bacteroides fragilis*

Nine isolates of *B. fragilis* from McGuire Veterans' Administration Hospital, Richmond, Va. were tested by the same method described above. None of the strains were inhibited by even the highest concentration of nisin used (32 µg/ml). The MIC of nisin for these strains is therefore 64 µg/ml or more. Similarly, as shown in Table 3, 23 isolates from the University of Florence (Italy) Hospital also showed relatively low sensitivity to nisin; the median MIC was >128 µg/ml.

This example demonstrates that nisin is unlikely to disrupt the normal bowel flora of humans. It further demonstrates that the activity of nisin alone against fastidious Gram-negative species cannot be predicted from existing data relative to other species.

TABLE 1

In vitro activity of nisin against 20 clinical isolates of *C. difficile*

| Strain number | Minimal inhibitory concentration (MIC) of nisin in µg/ml |
|---|---|
| Cd 82 | 0.13 |
| Cd 62 | ≦0.016 |
| Cd 30 | 0.13 |
| Cd 145 | 0.25 |
| Cd 180 | 0.25 |
| Cd 171 | 0.13 |
| Cd 162 | 0.13 |
| Cd 233 | 0.13 |
| Cd 146 | 0.25 |
| Cd 154 | 0.25 |
| Cd 144 | 0.13 |
| Cd 158 | 0.06 |
| Cd 234 | 0.13 |
| Cd 248 | 0.13 |
| Cd 232 | 0.13 |
| Cd 228 | 0.25 |
| Cd 240 | 0.25 |
| Cd 241 | 0.25 |

TABLE 1-continued

In vitro activity of nisin against 20 clinical isolates of C. difficile

| Strain number | Minimal inhibitory concentration (MIC) of nisin in µg/ml |
|---|---|
| Cd 243 | 0.25 |
| Cd 242 | 0.06 |

TABLE 2

Comparative activity of nisin against 60 clinical isolates of C. difficile

| Compound | MIC range | $MIC_{50}$ | $MIC_{90}$ |
|---|---|---|---|
| nisin | 0.03–1 | 0.05 | 0.25 |
| vancomycin | 0.13–2 | 0.38 | 0.8 |
| metronidazole | 0.25–4 | 0.35 | 0.8 |

All MIC values are in µml. $MIC_{50}$ and $MIC_{90}$ calculated geometrically.

TABLE 3

Comparative activity of nisin against 23 clinical isoiates of B. fragilis

| Compound | MIC range | $MIC_{50}$ | $MIC_{90}$ |
|---|---|---|---|
| nisin | 16->128 | >128 | >128 |
| clindamycin | 0.25->32 | 55 | 13 |
| metronidazole | 1->16 | 1.4 | 2 |

All MIC values are in µml. $MIC_{50}$ and $MIC_{90}$ calculated geometrically.

Example 2

Tolerability of Nisin in the Ligated Intestine of Rabbits

Five rabbits were anaesthetized and kept under narcolepsy for the entire experiment. The abdomen was incised and a segment of intestine including the ileo-cecal junction and the proximal colon was ligated. Two rabbits served as controls and three received 20 mg of bulk nisin (i.e., as received from the manufacturer) directly into the ligated segment of intestine. Rabbits were maintained for 6 hours before sacrifice.

At necropsy, and after histopathological examination of the exposed region of the intestine, there were no signs of irritation or toxicity attributable to treatment with nisin. This example shows that acute administration to the colon of rabbits of a dose of nisin similar to what might be administered to humans did not cause any local toxicity, even when the dose was artificially maintained in the colon for 6 hours by ligation of the intestine.

Example 3

Tolerability of Nisin upon Repeated Delivery to the Colon of Dogs

Dogs had tubes surgically implanted into the region of the proximal colon. After recovery, groups of 6 dogs were treated intracolonically, via the tube, with 0, 50, 125 or 300 mg/kg of bulk nisin per day for 28 days; the dosage was divided in half for administration at approximately 10 AM and 4 PM each day.

At necropsy, and after histopathological and clinical examinations, there were no signs of local irritation or of systemic toxicity attributable to treatment with nisin. This examples demonstrates that very high doses of nisin are tolerated after repeated administration to the colon of a mammal.

Example 4

Lack of Systemic Absorption of Nisin from the Colon

During the toxicological experiments described in Examples 2 and 3 above, blood samples were drawn for determination of nisin in serum.

In the rabbit ligated intestine model (Example 2) blood was drawn at 0.5, 2 and 6 hours after instillation of nisin. The method of analysis was a specific ELISA assay having a limit of quantitation of 1 µg/ml in rabbit serum.

No nisin was detectable in any of these samples, indicating that absorption from the colon, in this animal model, is negligible.

In the dog experiment (Example 3), blood samples were collected on day 28 at 0.5, 1, 2, 3, 4, 5, 6 and 7 hours after the morning dose of nisin. In this experiment, serum was assayed by a microbiological assay using Micrococcus luteus as the test organism; the limit of quantitation of this assay in dog serum is 0.5 µg/ml. Of the 18 dogs treated with nisin, 17 completed the study and 16 had correct catheter placement at necropsy. (Two dogs showed leakage of material into the peritoneum; one had to be sacrificed early during treatment and one completed the study.) For dogs that had correct (intra-intestinal) catheter placement, no nisin was detectable in the serum at any time point.

This example demonstrates that nisin, when correctly delivered to the colon of mammals, even at very high dosages, is not absorbed into the systemic circulation and is therefore highly unlikely to cause systemic toxicity.

Example 5

Nisin can Persist in the Colon of a Mammal at Concentrations Sufficient to Inhibit Target Bacteria.

In the rabbit experiment described above (Example 2), the contents of the intestinal loop were collected at necropsy. These were extracted and analyzed by HPLC. Intestinal contents of control rabbits, not treated with nisin, were used to estimate how well the extraction procedure worked. This was done by adding known quantities of nisin to these samples, homogenizing and extracting. The most efficient extraction procedure, which recovered about 50% of the added nisin, was then applied to the intestinal contents of the rabbits that had been treated with nisin. Up to 24% of the input nisin was recovered from the intestinal material of the treated rabbits, which means that, most likely, up to half of the nisin remained stable in situ for 6 hours.

Assuming a scale-up in dose to 600 mg of nisin per treatment in an adult human, and an average (full) colon content of approximately 4 liters, it should be possible to attain local concentrations as high as 40–80 µg/ml (or 40–80 µg/gm of colon contents) in the colon for extended periods. This is many times the MIC of the target organisms, C. difficile and Enterococcus spp., but at or below the limit of sensitivity of protective Gram-negative bowel flora such as B. fragilis. The actual dosage may be higher or lower, as it will of course depend on many factors, such as the efficiency of opening and dissolution of the dosage form in humans, the local bioavailability of the active ingredient (amount free to interact with bacteria vs. amount bound to solid material), the severity of the disease, the transit time of the product in individuals with diarrhea, and so forth. Accordingly, it is envisioned that multiple treatments (up to 6) may be given in any 24-hour period. The contemplated daily dosage ranges from a minimum of about 100 mg to a maximum of about 6 g, preferably from about 300 mg to about 2 g.

Since nisin is known to act very rapidly to kill susceptible bacteria, this example suggests that nisin or similar peptides, when delivered to the colon in sufficient dosages, can be used to treat bacterial disease due to susceptible bacteria or to eliminate potentially dangerous susceptible bacteria colonizing the intestine.

The above examples indicate that nisin and other peptides having similar antimicrobial properties would, contrary to expectations, have the desired effect in the environment of the colon and without any of the anticipated, possible undesirable effects.

Initially, formulations were devised to achieve delivery of therapeutic amounts of nisin to the colon via oral administration. Examples 6–8 are concerned with such formulations. What was sought in the studies below were dosage forms which could maintain their integrity for at least 4 hours at gastric pH and for 0.5–3 hours at pH 6.8 (that of the lower small intestine) and then begin to disintegrate in or near the vicinity of the colon.

Initial formulation studies were directed toward development of an uncoated core tablet which would rapidly disintegrate in phosphate buffer, pH 7.0. Formulation of the tablet core was not straightforward, because of the particular physico-chemical properties of nisin and the fact that the active drug makes up a relatively large proportion of the core tablet. Unlike most drug substances, including medicinal peptides, nisin is amphipathic (as well as being hydrophobic). Thus, although nisin is quite water soluble, even at neutral pH, it did not readily diffuse out of the compressed core when the core was immersed in buffer. Instead, a layer of gelled nisin formed around the tablet, which prevented access of water to the interior of the tablet. After an extensive formulation program to evaluate various excipients and disintegrants, this unique problem was solved only by incorporating an optimized amount of sodium chloride into the tablet. This decreased the gelling sufficiently to allow for tablet disintegration.

A second formulation problem encountered related to the strength of the core tablet. The tablet must be able to withstand the vigorous agitation encountered in the subsequent Wuster™ Fluidized bed coating process. Tablets containing various proportions of high efficiency binders (Povidone, Methocel and Carbopol™) had inadequate strength for this process. An in-depth evaluation led to the conclusion that because of the nature and physicochemical properties of nisin, binding was prevented due to entrapped air, thus leading to poor physical strength of the tablets. This problem was solved by introducing a roller compaction technique into the tabletting process.

Release characteristics of the formulation were imparted by coating the core tablets with methyacrylic acid:methylmethacrylate copolymers (Eudragit™). Time to beginning of tablet disintegration and time to completion of disintegration were reproducibly varied by application of differing coating weights to the core tablet.

Examples 6–11 are concerned with various formulations and the testing of their suitability for delivering effective amounts of the lanthocins of the instant invention to the colon.

Example 6a

Effect of Disintegrant on Tablet Disintegration
Core tablets were prepared containing the following components:

| Component | Percent of drug weight[1] |
|---|---|
| Bulk nisin | 100 |
| Sodium chloride | 10 |
| Disintegrant | 10 |
| Aerosil | 0.25 |
| Magnesium stearate | 1.0 |

[1] w/w relative to bulk nisin

Disintegrants used were Ac-Di-Sol, Explotab and Polyplasdone XL. Disintegration times (measured in phosphate buffer, pH 7) of tablets containing various disintegrants were:

| Disintegrant | Disintegration time (n = 3) |
|---|---|
| Ac-Di-Sol | 7.6 ± 0.4 min |
| Explotab | 9.1 ± 1.7 min |
| Polyplasdone XL | 9.7 ± 1.8 min |

Tablets formulated with Ac-Di-sol as the disintegrant disintegrated faster than tablets formulated with other tested disintegrants. Accordingly, subsequent formulations were prepared with Ac-Di-Sol.

Example 6b

Effect of NaCl on Tablet Disintegration
Core tablets were prepared containing the following components:

| Component | Percent of drug weight[1] |
|---|---|
| Bulk nisin | 100 |
| Sodium chloride (Fisher) | 0–20 |
| Ac-Di-Sol | 10 |
| Aerosil | 0.25 |
| Magnesium stearate | 1.0 |

[1] w/w relative to bulk nisin

Disintegration times (measured in phosphate buffer, pH 7) of tablets containing various amounts of sodium chloride were:

| % sodium chloride (w/w of core tablet) | Disintegration time (n = 3): |
|---|---|
| a) 0% sodium chloride: | No disintegration after 1.5 hours |
| b) 0.9% sodium chloride: | No disintegration after 1.5 hours |
| c) 2.6% sodium chloride: | 4.9 ± 0.4 min. |
| d) 4.2% sodium chloride: | 4.1 ± 0.1 min. |
| e) 8.3% sodium chloride: | 6.1 ± 0.5 min. |
| f) 15.3% sodium chloride: | 5.1 ± 0.2 min. |

The above demonstrates that the presence of sodium chloride in sufficient concentration overcomes the nisin gelling problem and greatly facilitates the disintegration of nisin tablets at physiological pH. The tested core tablets containing greater than 1% sodium chloride disintegrated in from 4–6 minutes, whereas at NaCl concentrations of 1% or less, no disintegration occurred even after 1.5 h. Furthermore, little change in disintegration time was seen with NaCl concentrations of up to 15.3%. According to the instant invention, formulations with NaCl concentrations ranging from about 2% to about 20% would be expected to effectively deliver nisin or another lanthocin to the colon.

Example 7

Nisin Core Tablets
Core tablet formulations containing the following components in the stated proportions were prepared and tested.

| Batch | Ac-Di-Sol[1] | Sodium chloride[1] |
|---|---|---|
| NIP (1) | 10% | 10% |
| NIP (2) | 15% | 15% |

[1]w/w relative to bulk nisin

| NIP (1) | |
|---|---|
| Formula: | (percents relative to bulk nisin) |
| Intragranular: | |
| Bulk nisin | 100 |
| Prosolv 90 | 12.5 |
| Ac-Di-Sol | 5 |
| Sodium chloride | 5 |
| Talc | 5 |
| Extragranular: | |
| Prosolv 90 | 12.5 |
| Povidone | 5 |
| Ac-Di-Sol | 5 |
| Sodium chloride | 5 |
| Magnesium stearate | 0.5 |
| Total tablet weight = 152.5 mg | |

Tablet properties:

Crushing strength=5.65±1.8 kp (n=10)

Disintegration time:

In R.O. (reverse-osmosis-purified) water=24.4±2.5 min. (n=3)

In phospate buffer pH=33.1±4.5 min. (n=3)

| NIP (2) | |
|---|---|
| Formula: | (percents relative to bulk nisin) |
| Intragranular: | |
| Bulk nisin | 100 |
| Prosolv 90 | 12.5 |
| Ac-Di-Sol | 7.5 |
| Sodium chloride | 7.5 |
| Talc | 2 |
| Extragranular: | |
| Prosolv 90 | 12.5 |
| Povidone | 5 |
| Ac-Di-Sol | 7.5 |
| Sodium chloride | 7.5 |
| Magnesium stearate | 0.5 |
| Total tablet weight = 162.5 mg | |

Tablet properties:

Crushing strength=5.56±1.89 kp (n=10)

Disintegration time:

In R.O. water=23.9±2.1 min (n=3)

In phospate buffer pH 7.0=29.9±2.7 (n=3)

Not only were the dosage forms found to have acceptable disintegration properties and desirable crushing strength when subjected to simulated conditions of passage through the gastrointestinal tract, but it was found that nisin integrity and content uniformity were maintained therein.

Example 8
(A) Preparation of core tablets

| | Ingredient | Intra-granular | Extra-granular | Weight | % w/w bulk nisin |
|---|---|---|---|---|---|
| 1 | Bulk nisin | × | | 600 g | 100.0% |
| 2 | Sodium chloride | × | | 45 g | 7.5% |
| 3 | AcDiSol[1] | × | | 60 g | 10.0% |
| 4 | ProSolv[2] | × | | 75 g | 12.5% |
| 5 | Talc | × | | 12 g | 2.0% |
| 6 | Sodium chloride | | × | 45 g | 7.5% |
| 7 | AcDiSol | | × | 60 g | 10.0% |
| 8 | ProSolv | | × | 75 g | 12.5% |
| 9 | Povidone[3] | | × | 30 g | 5.0% |
| 10 | Magnesium Stearate | | × | 3 g | 0.5% |

[1]AcDiSol = cross-linked sodium carboxymethyl cellulose
[2]ProSolv = silicified microcrystalline cellulose
[3]Povidone = polyvinylpyrrolidone Core tablets were prepared according to the following sequence of steps:

1. Sieve all ingredients separately through a #20 (0.0331") mesh screen.
2. Weigh out the intra-granular portions of nisin, NaCl, AcDiSol and ProSolv (ingredients #1–4). Combine in a suitable glass container.
3. Mix for 15 minutes in a Turbula mixer @ 50 rpm.
4. Weigh out the talc (ingredient #5). Add to the mixed material from step 3.
5. Mix for 3 minutes in the Turbula mixer @ 50 rpm.
6. Compact the mixture from step 5 in a roller compactor (Model TF-mini), roll pressure=100 kg/cm$^2$; roll speed=6 rpm; screw speed=11 rpm.
7. Pass the compacts from step 6 through a 1.0 mm mesh screen using an oscillating granulator (Erweka AR400 Wet-Dry Granulator).
8. Compact the granules from step 7 in a roller compactor, roll pressure=30 kg/cm$^2$; roll speed=8 rpm; screw speed= 11 rpm.
9. Pass the compacts from step 8 through a 1.0 mm mesh screen using an oscillating granulator.
10. Compact the granules from step 9 in a roller compactor, roll pressure=30 kg/cm$^2$; roll speed=8 rpm; screw speed= 11 rpm.
11. Pass the compacts from step 10 through a 1.0 mm mesh screen using an oscillating granulator.
12. Weigh out the extra-granular portions of NaCl, AcDiSol, Prosolv and Povidone (ingredients #6–9). Add to granules in step 11.
13. Mix for 10 minutes in the Turbula mixer @ 50 rpm.
14. Weigh out the magnesium stearate (ingredient #10). Add to the mixture from step
15. Mix for 2 minutes in the Turbula mixer @ 50 rpm.
16. Compress the mixture from step 15 in a Manesty D3B rotary tablet press (compression pressure=1500 pounds; speed=16 rpm) using 7.0 mm bioconcave stations.

The core tablets prepared in this way were found to have the strength required to maintain their integrity during the subsequent coating process.

(B) Preparation of coated tablets

| | Ingredient | Weight | % w/Eudragit polymer[1] |
|---|---|---|---|
| 1 | Eudragit L30D-55 | 1 kg | — |
| 2 | Triethyl citrate | 45 g | 15.0% |
| 3 | Sterile water | 500 g | 166.7%[2] |
| 4 | Talc | 6 g | 2.0% |

[1]Dispersion is 30% solid polymer (i.e., 30 g solid polymer/100 g dispersion).
[2]Water is added to make dispersion 20% (i.e., 50% of Eudragit L30D-55 dispersion weight).

A dispersion for coating of the core tablets prepared as in (A) above was prepared according to the following steps:
1. Filter Eudragit L30D-55 through a clean mesh screen.
2. Weigh out Eudragit L30D-55 dispersion.
3. Weigh out water. While stirring, add approximately ⅔ of the water to the Eudragit dispersion.
4. Weigh out triethyl citrate (TEC). While stirring, add TEC dropwise to the Eudragit dispersion. Wash the TEC container with the remainder of the water (in 2 portions) and add to the mixture.
5. Stir for 1 hour.
6. Weigh out talc. While stirring, add to the mixture.
7. Stir for 1.5 hours.

The core tablets were coated with the coating dispersion according to the following steps:
1. The core tablets were placed in a fluidized bed Wurster attachment.
2. The coating dispersion was placed on a balance allowing continuous stirring using a magnetic stirrer.
3. The core tablets were coated using the following coating conditions:
   Spraying rate: 7.0 gm/min
   Atomization pressure: 1.5 bar
   Inlet temperature: 50° C.

Example 9

Effect of Coat Thickness on Tablet Disintegration

Figure 2:
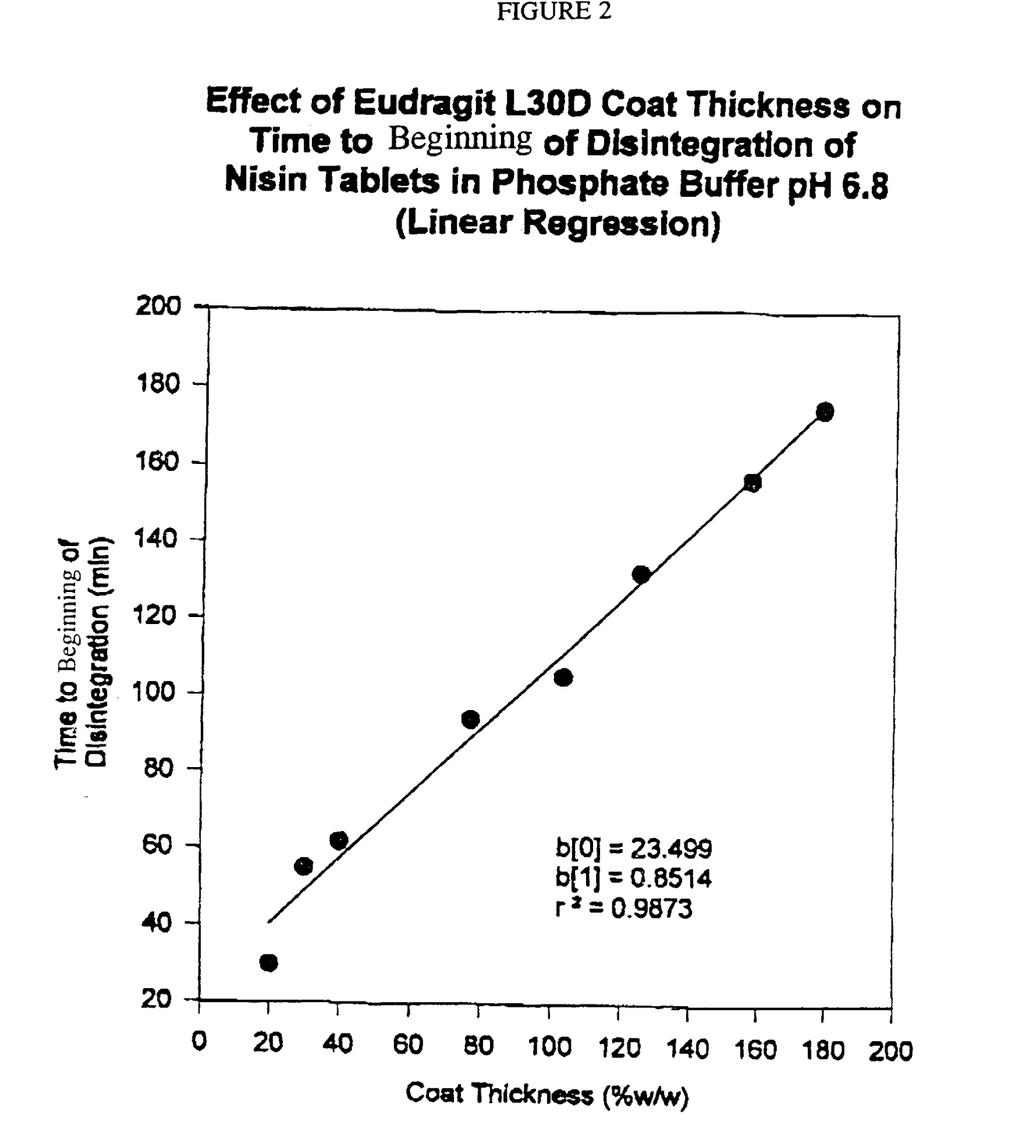
FIG. 2 shows the effect of tablet coat thickness on the time to onset of tablet disintegration in phosphate buffer.
Figure 3:
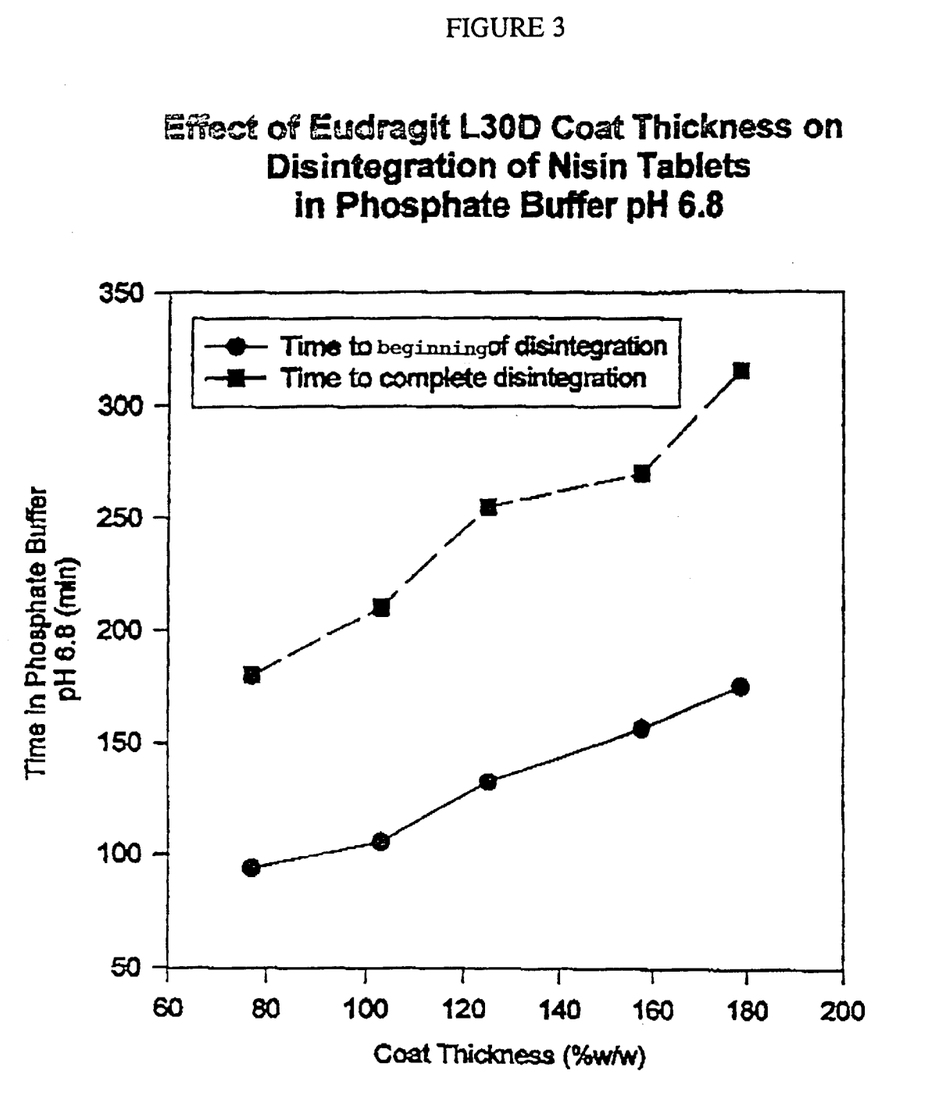
FIG. 3 shows the effect of tablet coat thickness on both the time to onset and time to completion of tablet disintegration in phosphate buffer.
Figure 4:
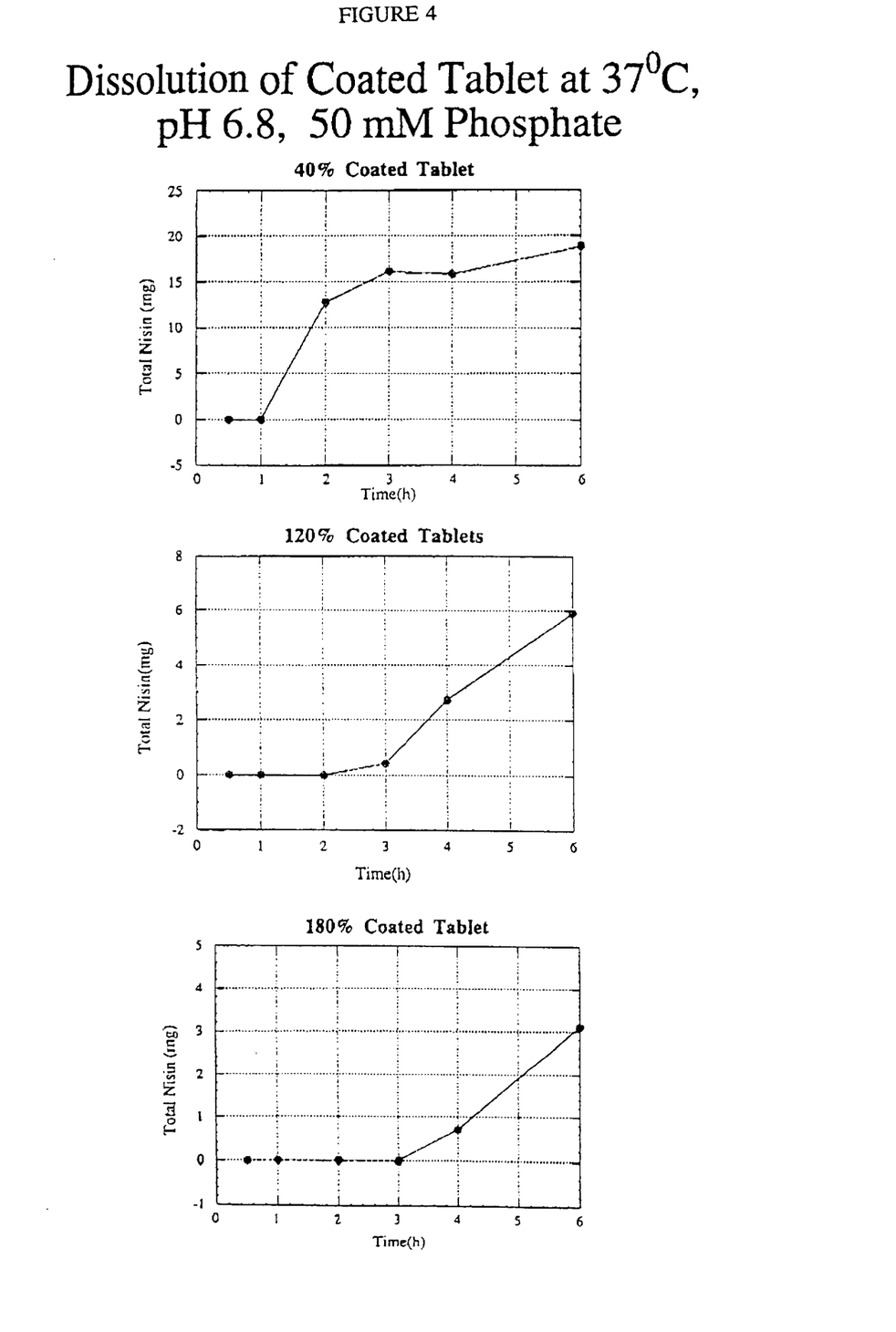
FIG. 4 shows the effect of coating thickness on the delay of nisin release into pH 6.8 phosphate buffer.

The effect of Eudragit L30D coat thickness on disintegration and dissolution at pH 6.8 of tablets so coated was tested. Coat thickness percentage is the ratio of weight of coating to weight of core tablet. The results shown in FIGS. 2 and 3 demonstrate that both the time to onset and time to completion of disintegration are essentially proportional to Eudragit L30D coat thickness. The results presented in FIG. 4 show that the time lag between initial contact of the tablet with the buffer and initial release of nisin is directly related to the coating thickness. Thus, delayed release characteristics sufficient to deliver a drug to the colon via oral administration can be imparted by employing an Eudragit L30D coating of sufficient thickness. Furthermore, the delayed release characteristics can be varied by manipulation of the coating thickness.

According to the instant invention, coat thicknesses in the range from about 20% to about 180% (0.15 mm to 1.316 mm measured axially) would be expected to provide desirable delayed release characteristics of the formulations. A thickness of about 40% (0.371±0.07 mm measured axially) is the best embodiment of the invention presently known.

Example 10

Figure 5:
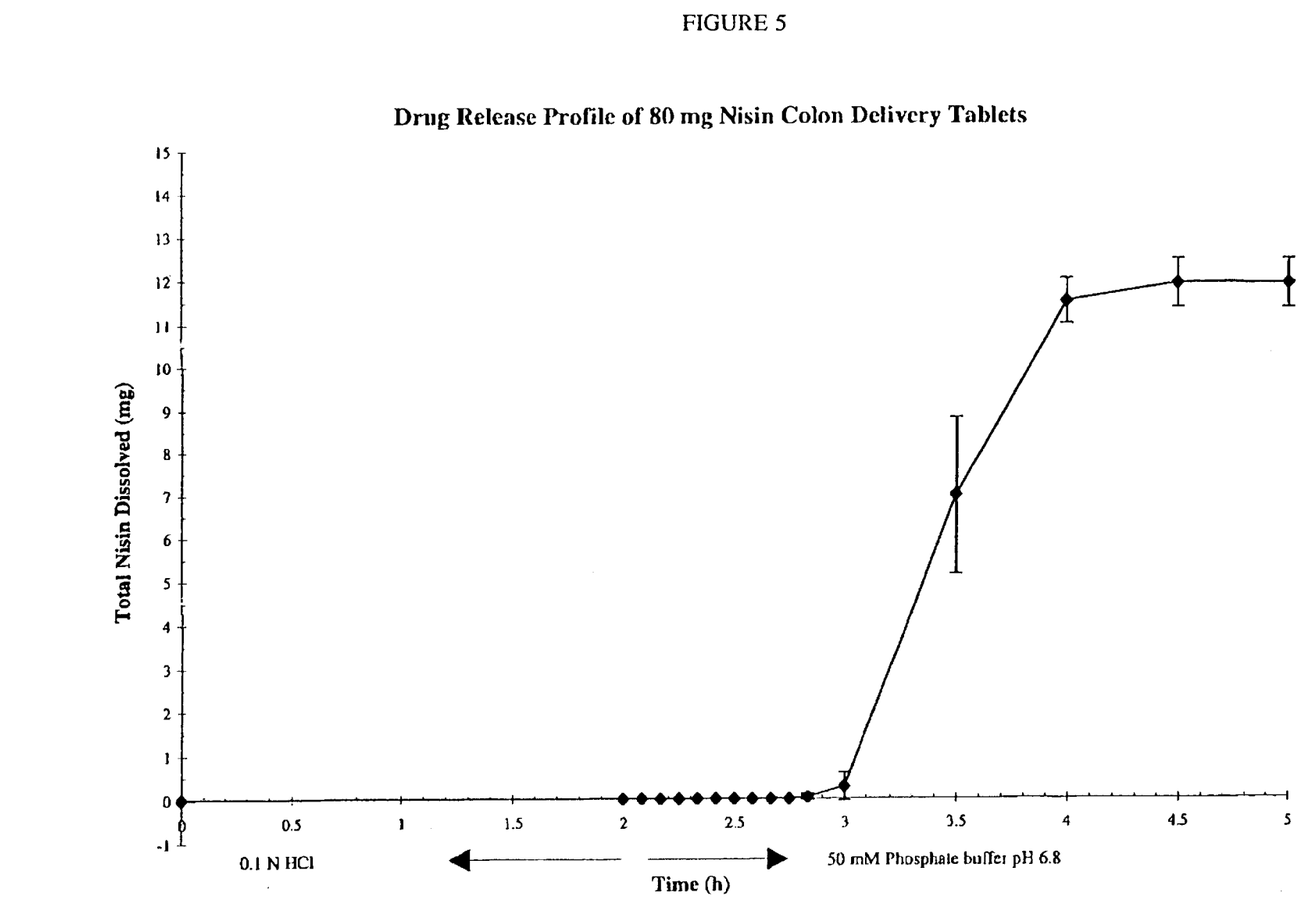
FIG. 5 shows the drug dissolution profile of 6 tablets with a 40% Eudragit™ coating.

Drug Release under Simulated Conditions of Passage through the Gastrointestinal Tract Tablets (6) with a 40% Eudragit L30D coating (0.371 mm coat thickness measured axially) were prepared using a USP type II apparatus in pH 6.8 buffer at 37° C. using a stir speed of 100 rpm. A dissolution profile for the tablets was obtained by first subjecting the tablets to a 0.1N HCl (stomach) environment followed by a 50 mM phosphate buffer pH 6.8 (large intestine) environment. The results, presented in FIG. 5, show that nisin tablets can be prepared that reproducibly release nisin with delay times desirable for delivery to the human colon.

Example 11

Demonstration of Delivery of Nisin to the Colon of a Human Subject using a Delayed Release Tablet Core tablets containing 100 mg bulk nisin were formulated with the proportions of active ingredient and excipients described in Example 8 above, except that, in addition, samarium oxide was included to the extent necessary to be present in the amount of 10 mg per tablet. Core tablets were coated with Eudragit L30D-55 as in Example 8 to 40% of core tablet weight (0.371 mm coat thickness measured axially). Additional core tablets were coated to 120% (0.896 mm coat thickness measured axially) and 180% (1.316 mm coat thickness measured axially) of core tablet weight. Tablets were then subjected to neutron bombardment. This converts a portion of the nonradioactive samarium ($^{152}$Sm) to radioactive $^{153}$Sm, which allows imaging of the tablet in the gastrointestinal track using scintigraphy [Digenis, G. A., and Sandefer, E. Gamma Scintigraphy and Neutron Activation Techniques in the In Vivo Assessment of Orally Administered Dosage Forms, Crit. Rev. Ther. Drug Carrier Systems 7 309–345 (1991)].

A scintigraphy study was performed using twelve healthy male human subjects. In the first session, six subjects each received a single neutron-activated tablet coated with either 40%, 120% or 180% Eudragit (two subjects per formulation). In the second session, 4 subjects received a single 40% tablet and 2 subjects received a single 120% tablet. Tablets were swallowed with 250 ml ice water. Imaging was performed at intervals of 30 minutes.

Figure 6A:
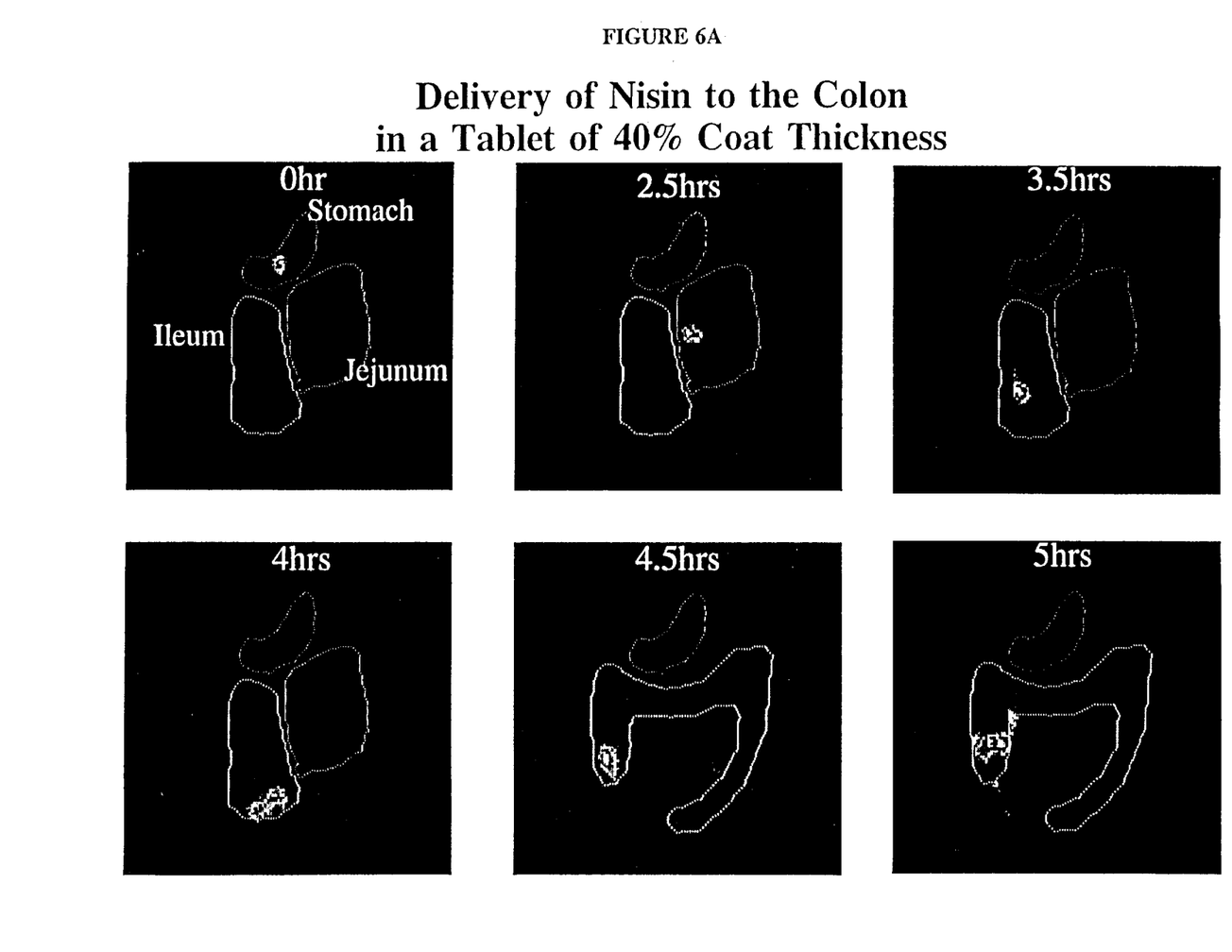
FIGS. 6A and 6B show the progress of a tablet formulation of 40% coat thickness through the human gastrointestinal tract over the course of 7 hours following ingestion.
Figure 6B:
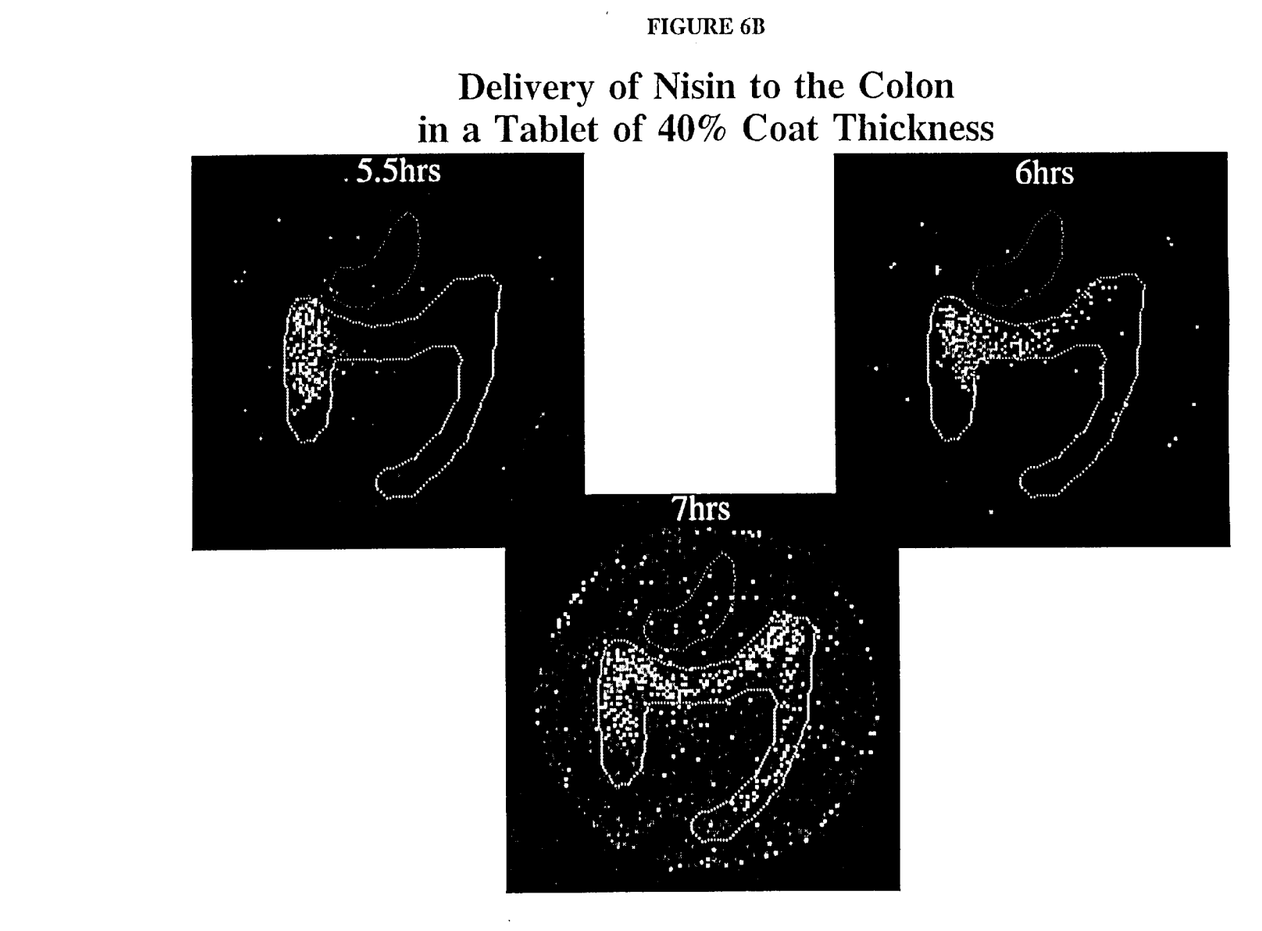
Figure 7A:
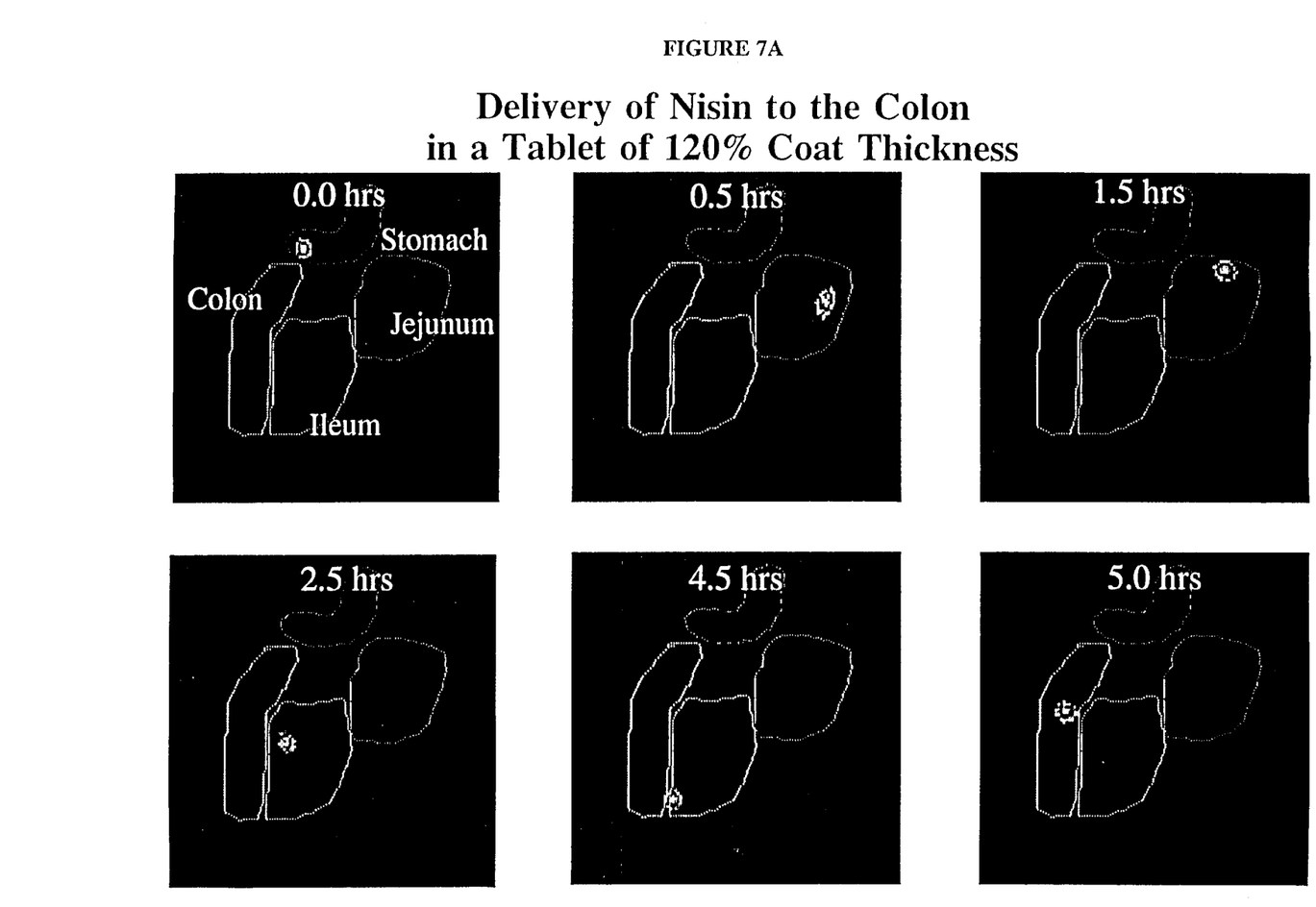
FIGS. 7A and 7B show the progress of a tablet formulation of 120% coat thickness through the human gastrointestinal tract over the course of 12 hours following ingestion.
Figure 7B:
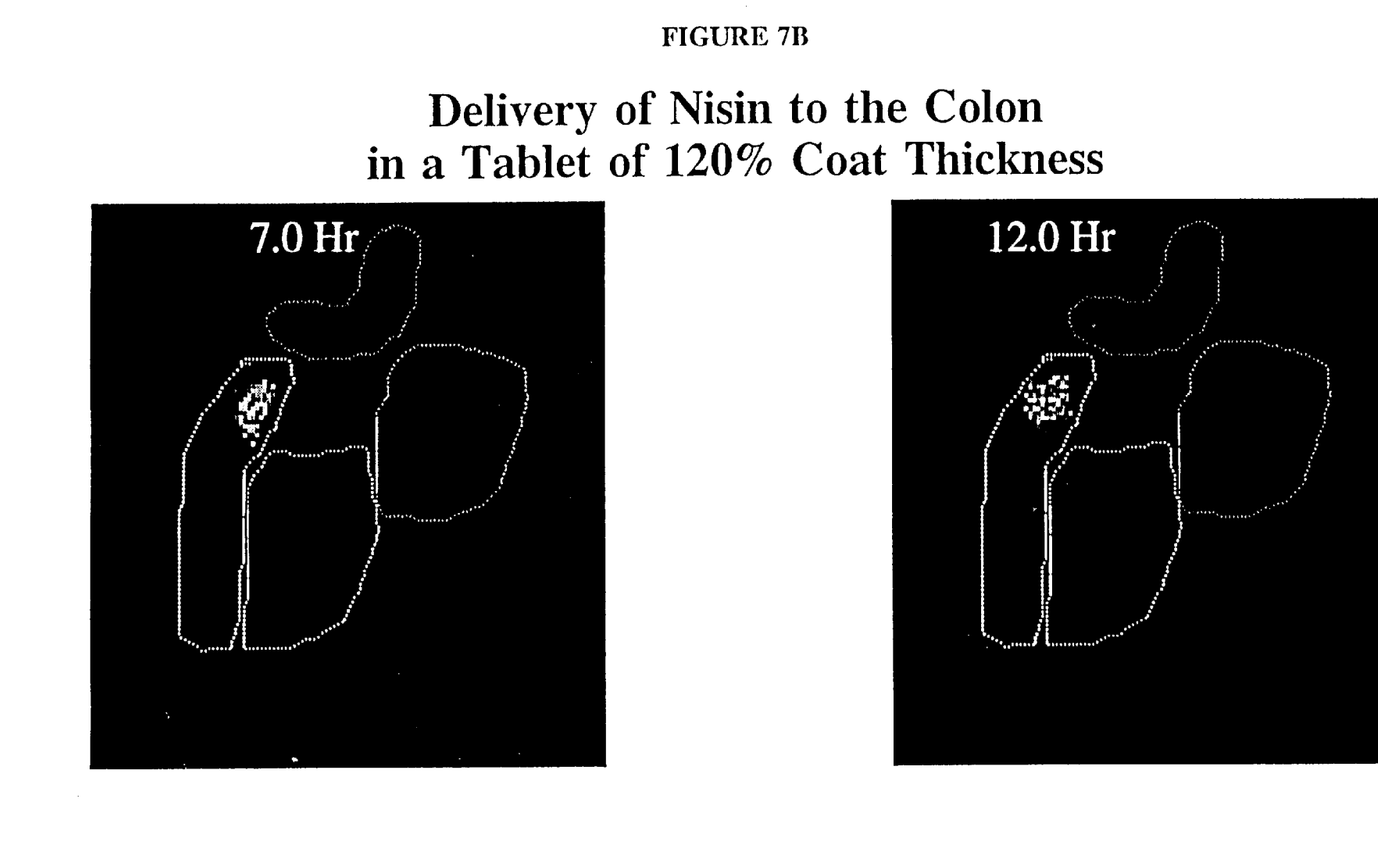
Figure 8A:
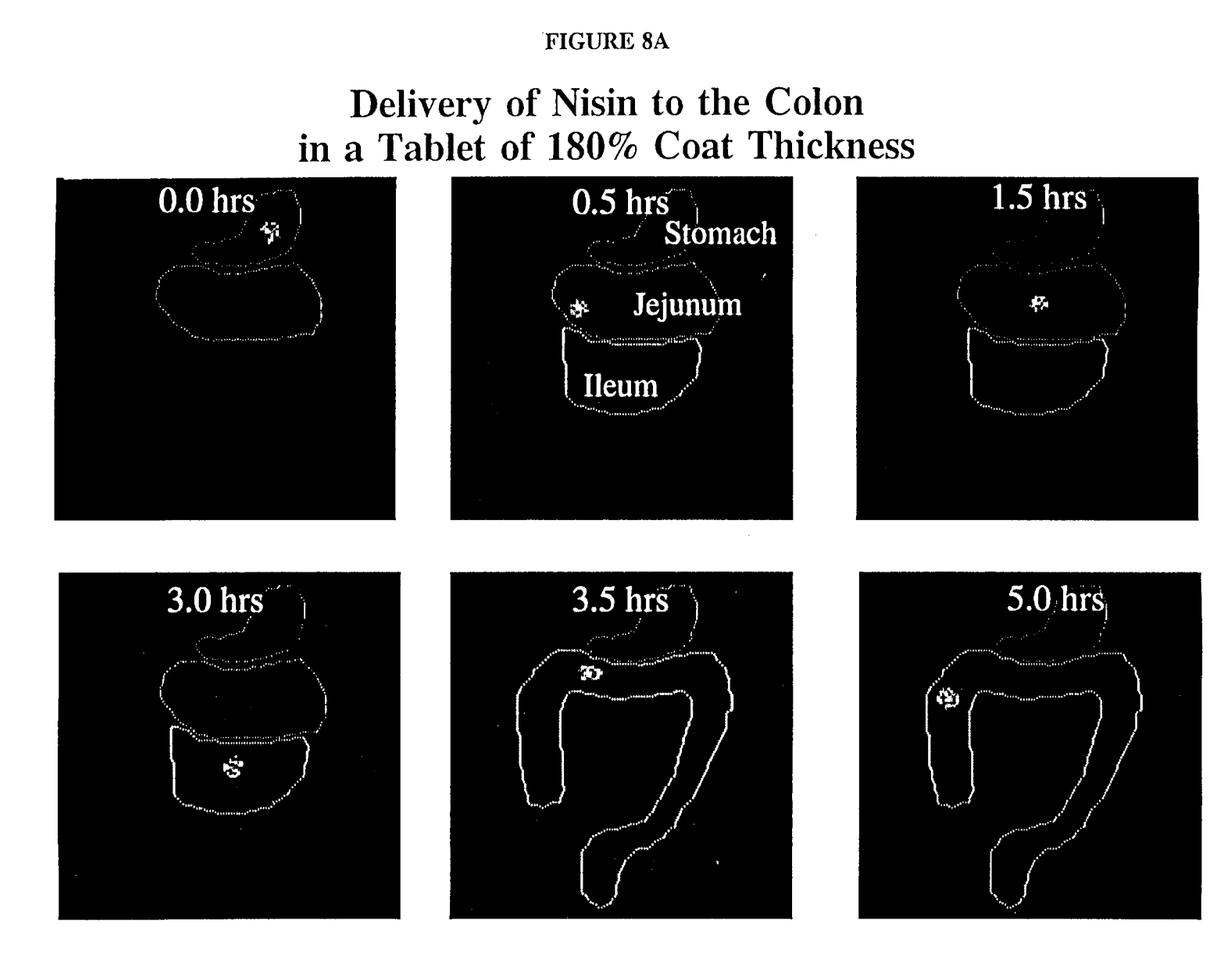
FIGS. 8A and 8B show the progress of a tablet formulation of 180% coat thickness through the human gastrointestinal tract over the course of 16 hours following ingestion.
Figure 8B:
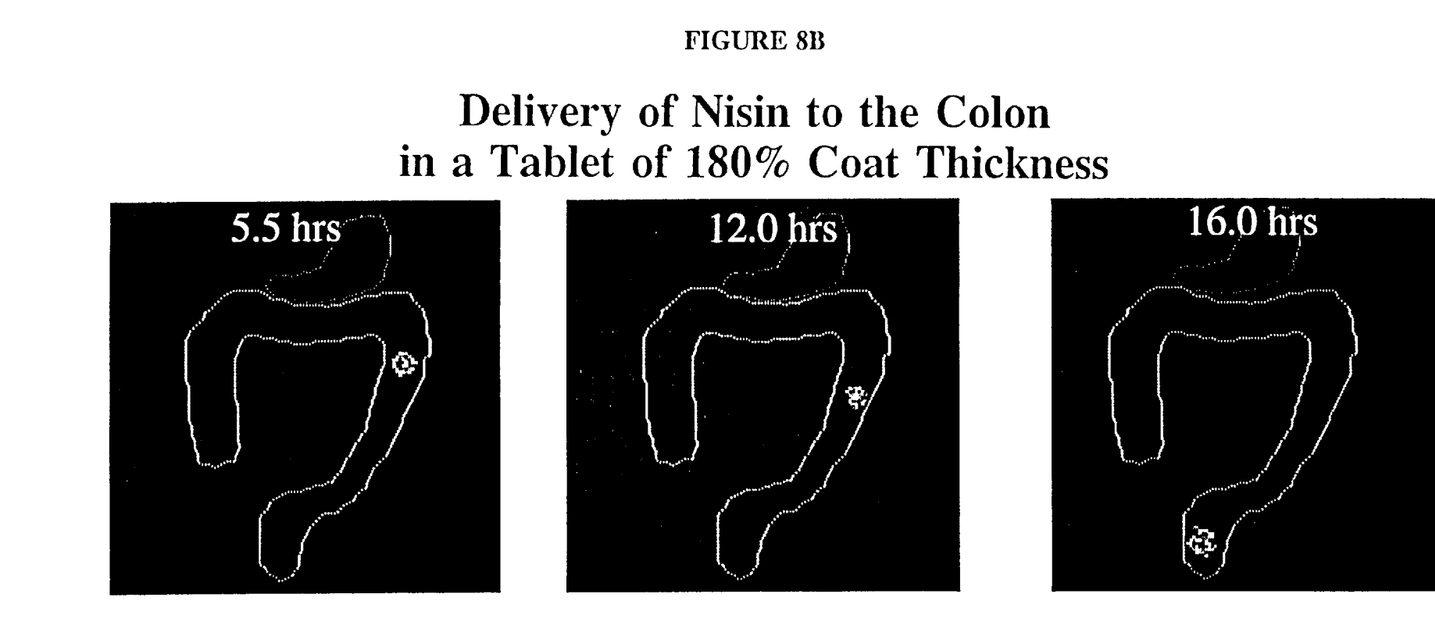

FIGS. 6–8 demonstrate the fates of different tablet formulations as they progressed through the gastrointestinal tract. FIGS. 6A and 6B demonstrate the progress of a 40% tablet in one subject, FIGS. 7A and 7B demonstrate the progress of a 120% tablet, and FIGS. 8A and 8B show the progress of a 180% tablet. In FIG. 6A it can be seen that the 40% tablet remains intact throughout the stomach and jejunum. The tablet is completely disintegrated in the proximal colon at 5.5 h (FIG. 6B). The 120% tablet is just beginning to disperse at 12 h, at which point it is in the transverse colon (FIG. 7B). The 180% tablet has reached the rectum essentially intact (FIG. 8B). These results demonstrate that the timing of the tablet dispersion in vivo as well as in vitro is related to the thickness of the coating.

Data from the 6 subjects receiving the 40% tablet are summarized in Table 4. In 5 of the 6 subjects, the onset of tablet disintegration occurred between the distal ileum and transverse colon with progressive dispersal throughout the colon.

TABLE 4

Disintegration of 40%-Coated Nisin Tablets in Human Subjects

| Subject # | Site of Initial Tablet Disintegration |
|---|---|
| 006 | mid to distal ileum |
| 012 | distal ileum/ascending colon |
| 003 | ileocecal junction/terminal ileum |
| 011 | ascending colon |
| 008 | ascending/transverse colon |
| 009 | descending colon |

Adverse effects were not observed in any of the 6 subjects who received this formulation.

This example demonstrates that nisin can be formulated in a tablet with appropriate release characteristics for local treatment of human disease of the colon, that dispersion of the tablet contents can be achieved in the human colon, and that a dose of 100 mg bulk nisin is well tolerated when administered to the colon of humans using a delayed release formulation. According to the invention, tablets containing from about 50 mg to about 600 mg nisin are contemplated. Multiple tablets (up to 4) may be administered in any given treatment and multiple treatments (up to 6) may be given in any 24-hour period. Daily dosages of nisin may range from a minimum of about 100 mg to a maximum of about 6 g, preferably from about 300 mg to about 2 g. Similar tablet doses and daily dosages are also contemplated for other lanthocins.

What is claimed is:

1. A process for preparing an orally administered formulation for release of a lanthanocin in the colon which comprises the steps of:
   (a) preparing a core tablet comprising a lanthanocin and a pharmaceutically-acceptable salt in an amount sufficient to prevent gelling of the lanthanocin in the environment of the gastrointestinal tract;
   (b) preparing the core tablet so as to confer sufficient strength to it to withstand a rigorous coating process; and
   (c) coating the core tablet with a coating of sufficient thickness and of a material having a pH dissolution profile that together provide delayed release characteristics that allow the tablet to arrive in intact form into the area of the colon with subsequent release of the lanthanocin in the colon.

2. A process according to claim 1 wherein the lanthocin is nisin.

3. A process according to claim 1 wherein the amount of salt is in the range from about 2% to about 20% w/w based on the weight of the core tablet.

4. A process according to claim 1, 2 or 3 wherein the salt is sodium chloride.

5. A process according to claim 1 wherein the strength of the core tablet is conferred by the use of 3 roller compaction steps.

6. A process according to claim 1 wherein the coating material is a methacrylic acid; methylmethacrylate co-polymer.

7. A process according to claim 6 wherein the coating material has a thickness in the range from about 0.15 mm to about 1.316 mm measured axially.

8. A process according to claim 1 wherein the lanthocin is present in the range from about 50 mg to about 600 mg; the amount of salt is in the range from about 2% to about 20% w/w based on the weight of the core tablet; the strength of the core tablet is conferred by the use of 3 roller compaction steps; and the coating material is Eudragit L30D in a coating thickness in the range from about 0.15 mm to about 1.316 mm measured axially.

9. A process according to claim 8 wherein the lanthocin is nisin.

10. A process according to claim 9 wherein the salt is sodium chloride.

11. A process according to claim 9 wherein the nisin is present as 100 mg bulk nisin.

12. A process according to claim 10 wherein the nisin is present as 100 mg bulk nisin.

13. A process according to claim 12 wherein the coating thickness is 0.371±0.07 mm measured axially.

14. A process according to claim 13 wherein the core tablet contains 15% sodium chloride and further comprises 20% AcDiSol, 25% ProSolv, 2% talc, 5% povidone and 0.5% magnesium stearate, all measured as % w/w relative to bulk nisin.

15. A formulation prepared by the process of any one of claims 1–3 and 5–14.

16. A formulation prepared by the process of claim 4.

17. A pharmaceutical composition for oral administration which releases lanthanocin in the colon, which comprises a core tablet comprising a safe and effective amount of lanthanocin and a pharmaceutically-acceptable salt in an amount sufficient to prevent gelling of the lanthanocin in the gastrointestinal tract, said core tablet formulated so as to have sufficient strength to withstand a rigorous coating process, said core tablet coated with a coating of sufficient thickness and of a material having a pH dissolution profile that together provide delayed release characteristics that allow the tablet to arrive in intact form into the area of the colon with subsequent release of the lanthanocin in the colon.

18. The pharmaceutical composition according to claim 17 wherein from about 50 mg to about 600 mg of lanthanocin is present in the core tablet; the salt is sodium chloride and is present in the range of from about 2% to about 20% based on the weight of the core tablet, and the coating material is a methacrylic acid; methylmethacrylate co-polymer, said coating having a thickness of from about 0.15 mm to about 1.316 mm measured axially.

* * * * *